United States Patent
Young et al.

[11] Patent Number: 6,141,038
[45] Date of Patent: Oct. 31, 2000

[54] ALIGNMENT CORRECTION PRIOR TO IMAGE SAMPLING IN INSPECTION SYSTEMS

[75] Inventors: Scott A. Young, Soquel; Roger Kroeze, Tracy; Curt H. Chadwick, Los Gatos; Nicholas Szabo, Cupertino; Kent E. Douglas, San Martin; Fred E. Babian, Boulder Creek, all of Calif.

[73] Assignee: KLA Instruments Corporation, San Jose, Calif.

[21] Appl. No.: 08/884,466

[22] Filed: Jun. 27, 1997

Related U.S. Application Data

[63] Continuation of application No. 08/538,137, Oct. 2, 1995, abandoned.

[51] Int. Cl.[7] .................................................. H04N 7/18
[52] U.S. Cl. .............................................. 348/87; 348/126
[58] Field of Search ................................ 348/87, 61, 86, 348/88, 92, 94, 95, 125–130; H04N 7/18

[56] References Cited

U.S. PATENT DOCUMENTS

| | | | |
|---|---|---|---|
| 3,851,951 | 12/1974 | Eveleth | 350/161 |
| 4,247,203 | 1/1981 | Levy et al. | 356/398 |
| 4,579,455 | 4/1986 | Levy et al. | 356/394 |
| 4,618,938 | 10/1986 | Sandland et al. | 348/126 |
| 4,644,172 | 2/1987 | Sandland et al. | 250/548 |
| 4,805,123 | 2/1989 | Specht et al. | 364/559 |
| 4,926,489 | 5/1990 | Danielson et al. | 382/8 |
| 5,502,306 | 3/1996 | Meisburger et al. | 250/310 |
| 5,563,702 | 10/1996 | Emery et al. | 356/73 |
| 5,572,598 | 11/1996 | Wihl et al. | 382/144 |
| 5,578,821 | 11/1996 | Meisberger et al. | 250/310 |

*Primary Examiner*—Young Lee
*Attorney, Agent, or Firm*—Allston L. Jones

[57] ABSTRACT

A method and apparatus, and variations of each, for inspecting a wafer defining at least one die thereon is disclosed. The present invention first obtains the electronic image equivalent of two die, and then determines the x and y offset between those electronic images. Prior to inspection for defects, those two electronic images are aligned by adjusting the x and y positions of one electronic image of one die with respect to the electronic image of the other die. Once that is accomplished, those electronic images are compared to detect any defects that may exist on one of the die.

28 Claims, 8 Drawing Sheets

ALIGNMENT CORRECTION PRIOR TO IMAGE SAMPLING IN INSPECTION SYSTEMS

This is a continuation of application of Ser. No. 08/538,137 filed on Oct. 2. 1995, abandoned.

FIELD OF THE INVENTION

The present invention is related to sub-pixel image alignment in wafer inspection machines, particularly to the alignment of images both prior to and subsequent to scanning. Two alternate methods are taught, one for laser scanning and the other for scanning with a linear array.

BACKGROUND OF THE INVENTION

It is well known in the wafer inspection art that when two similar images are to be compared, sub-pixel alignment is often necessary to obtain the degree of accuracy that is desired. Traditionally that alignment was accomplished by digitally interpolating the image after scanning.

The most frequently used method for automatic inspection of photomasks or patterned semiconductor wafers utilizes comparison to detect defects. Typically, two supposedly identical patterns are compared by scanning and digitizing the images. The digitized images are then compared in high speed digital logic, or an image is compared with data stored in the CADS (Computer Aided Design System) database with data representing the desired pattern.

In the comparison process to detect differences between the two patterns some form of image subtraction is most frequently employed. However, image subtraction is contingent on sampling the two images (or the image and image data from the database) at nearly identical points for both images.

Early mask inspection systems, such as taught by Levy, et al., in U.S. Pat. No. 4,247,203, were able to guarantee only a ±2½ pixel registration accuracy between the two images. Because of the limited registration accuracy, Levy required that the defect detection algorithm use feature extraction, followed by the matching of these features, rather than image subtraction. Some time later Levy, U.S. Pat. No. 4,579,455, taught area subtraction, but because of the limited registration accuracy computed the intensity difference at several possible registrations. If, for any of these registrations the absolute value of the intensities was less than a predetermined threshold, no defect was recorded at that particular pixel. Subsequently, Specht, et al., in U.S. Pat. No. 4,805,123, taught a method of achieving image subtraction by first reducing the registration error between the two images to less than a pixel. However, the Specht method had the shortcoming that in re-registering (also known as resampling) the two images with respect to each other, interpolation of the scanned image was used, which in turn introduced errors in determining the intensities of the resulting pixels. These errors limited sensitivity (the smallest detectable defect).

As will be shown subsequently, the maximum intensity error determines the maximum detectable defect-to-pixel ratio. Since inspection speed, at a given sensitivity, defines the productivity of an inspection system, for a fixed sampling rate, it is desirable to maximize the pixel size. Therefore, to achieve the maximum throughput, one must minimize the registration error. The present invention teaches methods for minimizing the registration error for the two most common scanning methods: scanning with a laser and scanning with a linear array.

SUMMARY OF THE INVENTION

The present invention is a method and apparatus, and variations of each, for inspecting a wafer defining at least one die thereon. The present invention first obtains the electronic image equivalent of two die, and then determines the x and y offset between those electronic images. Prior to inspection for defects, those two electronic images are aligned by adjusting the x and y positions of one electronic image of one die with respect to the electronic image of the other die. Once that is accomplished, those electronic images are compared to detect any defects that may exist on one of the die.

DETAILED DESCRIPTION OF THE PRESENT INVENTION

The key to the present invention is the use of the same sampling points for both images, or the image of the die being viewed and the die equivalent in the data base, to be compared as will be seen from the following discussion.

Figure 3A:
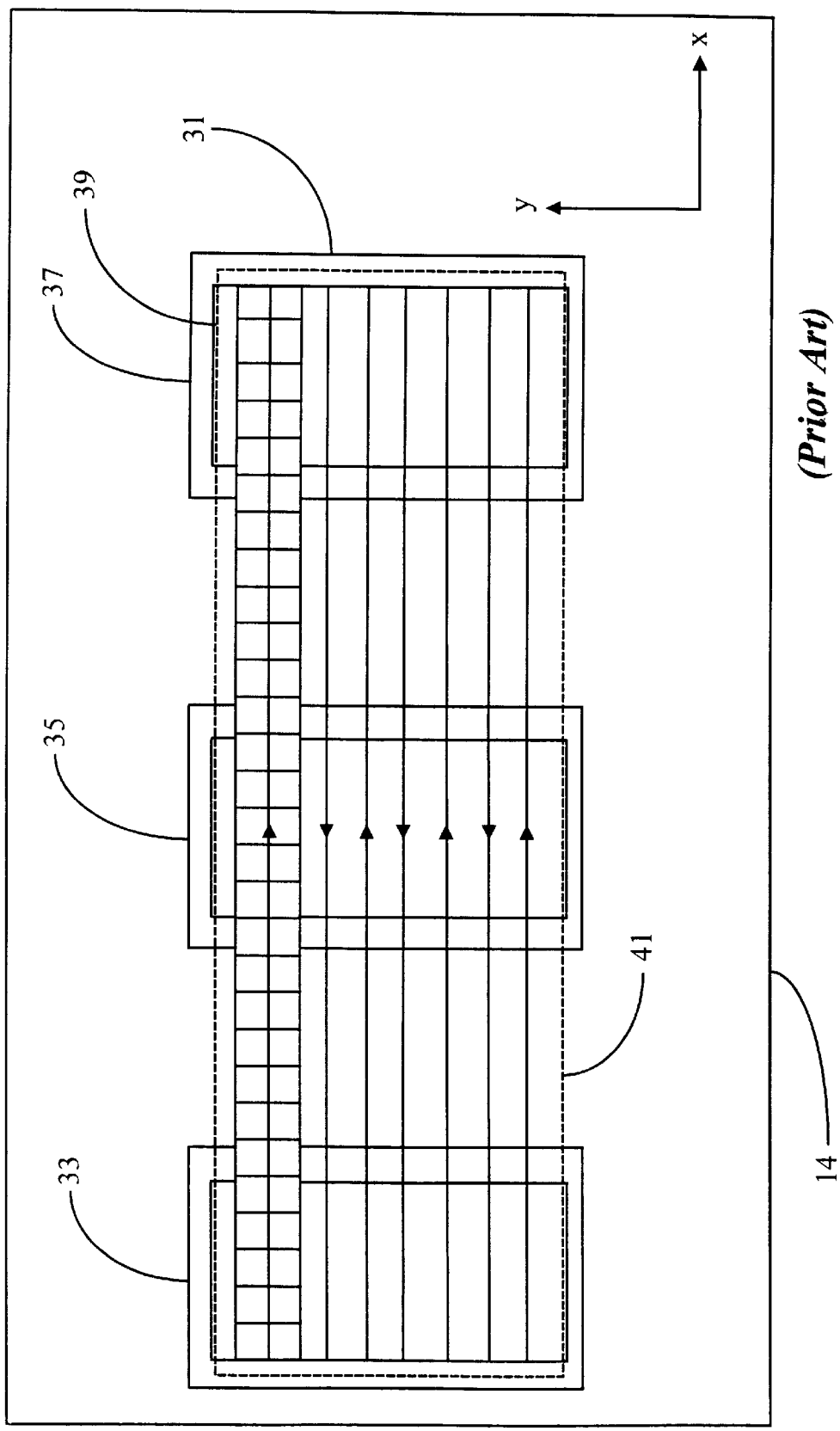
FIG. 3a illustrates the scanning of multiple patterns from die-to-die inspection.
Figure 3B:
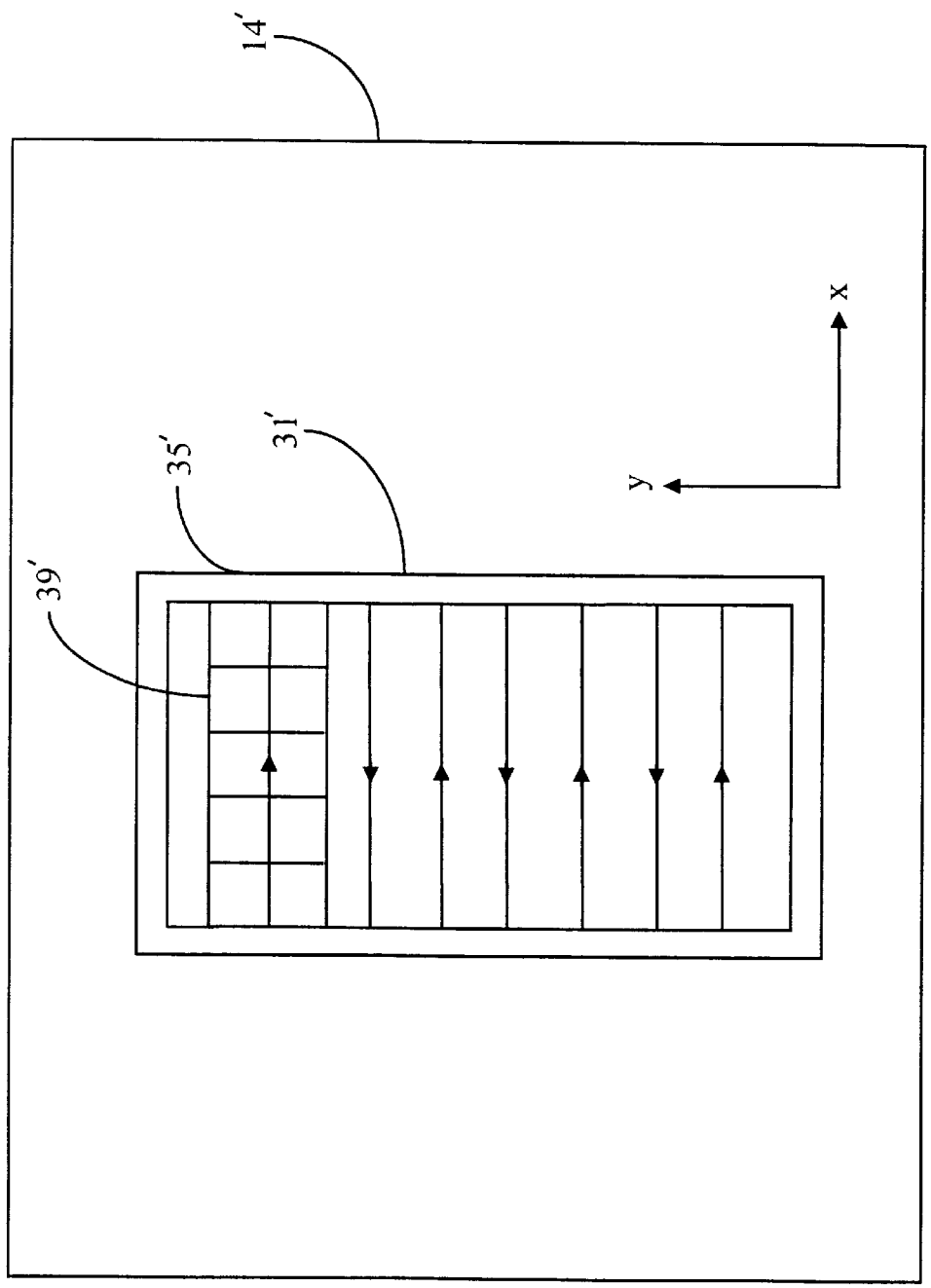
FIG. 3b illustrates the scanning of a single pattern for die-to-database inspection.

FIGS. 3a and 3b illustrate the typical serpentine scanning technique for multiple patterns and for a single pattern, respectively. In FIG. 3a wafer 14 is scanned in a serpentine path 31, sweeping out several dies 33, 35 and 37 in die-to-die inspection, and in FIG. 3b only a single die is scanned in serpentine path 31' when die-to-database inspection is employed. Each sweep of the path is designated a swath. A typical swath may have a height of 500 to 2,000 pixels and may have a length of 500,000 pixels.

Figure 1:
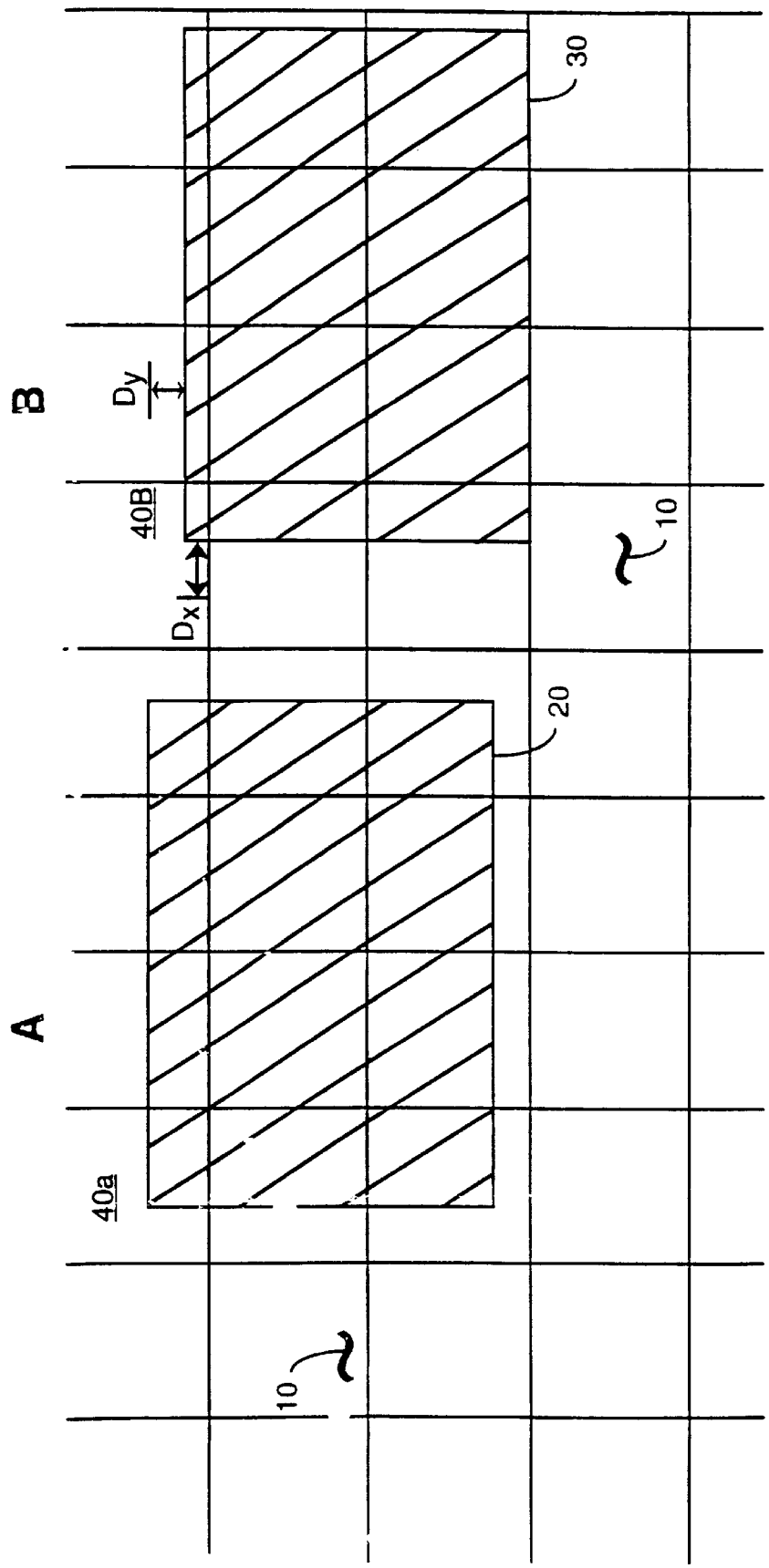
FIG. 1 illustrates the pixelization of a surface by an inspection system and the mis-alignment between two images.

FIG. 1 illustrates two identical forms 20 and 30 superimposed on a grid that represents the boundaries of pixels 10 as defined by the inspection system of the present invention. The nominal sampling point of each pixel is the center of that pixel. However, in reality the scanner measures the total light energy that falls on an area of approximately the size of a pixel 10. The idealized intensity value of each pixel is the normalized intensity value expressed as a percentage of the maximum. FIG. 1 shows two identical geometric forms 20 and 30, each consisting of a rectangle of opaque material (e.g., chromium) on a transparent medium, such as quartz. In this configuration, pixels 40A and 40B have different measured values since the sampling points (the centers of the pixels) are not equidistant from the corresponding one of two forms 20 and 30, respectively. Consequently, pixels 40A and 40B, as shown in FIG. 1 have measurable values of 76% and 92%, respectively.

Clearly, if pixel-to-pixel comparison is used for defect detection, the sampling points must nearly coincide with respect to the forms. It can readily be seen that the registration error (the relative displacement of the sampling points between the two forms 20 and 30) determines the maximum possible intensity difference between any two pixels to be compared. Assuming that $\Delta I$ is the maximum possible intensity difference attributable to the registration error, then the defect detectors intensity threshold must be at least $\Delta I$. For binary images, i.e. where at every sampling point the transmittance is either 0 or 100%, the minimum detectable defect size (in terms of area) is merely $D_x$ times $D_y$, where $D_x$ and $D_y$ are the maximum x and y directional registration errors (see FIG. 1 for the $D_x$ and $D_y$ between forms 20 and 30 for example).

In the prior art, as stated above in the Background of the Invention section, registering the two images was accomplished by first scanning both images. Next, integer pixel misalignment was corrected as taught by Levy, by shifting the image in the digital memory the appropriate number of locations. Fractional pixel registration was achieved by resampling one of the images as taught by Specht.

In the present invention, for both scanning techniques, a coarse correction is made prior to sampling, the image is scanned and then stored in memory. For diode array scanning (FIG. 2) coarse correction in the X-direction is implemented by a mechanical movement of a mirror, while for laser scanning (FIG. 4) X-directional coarse correction uses timing control of the sampling. In the Y-direction, both scanning techniques use timing control of the sampling.

The purpose of the present invention is to minimize the intensity error caused by the registration error of sampling points with respect to the two forms to be compared whether die-to-die or die-to-data base.

The present invention is an improvement over the Specht method in that a coarse correction of the misregistration error is achieved in both X and Y prior to the scanning of the pattern, or patterns. The residual error after coarse correction and subsequent to scanning is then further reduced by interpolation of the intensities. Since the residual alignment error after coarse correction is now small, the error contributed by interpolation is significantly smaller than when the Specht alignment and inspection method is used. Hence, with the present invention, the two images used in image subtraction are much better aligned with respect to each other and consequently the minimum detectable defect, as a percentage of the pixel size, is significantly smaller than as in the prior art. Consequently, a larger pixel size can be used for a given minimum detectable defect. A larger pixel size, for a given minimum detectable defect and for a constant pixel rate translates into a higher throughput than in the prior art. Higher throughput produces more defect data which in turn results in more reliable diagnosis of the problems and better yield management.

One significant concept of the present invention is that one may employ a pixel that is significantly larger than the minimum detectable defect or even the minimum feature size (geometric figure on the mask or wafer), provided the two images are registered accurately with respect to each other.

The present invention relates to two different scanning embodiments and how improved registration may be achieved using the present invention. These scanning embodiments are: Scanning with a Diode (or TDI) Array, and Scanning with a Laser Beam. These two embodiments are discussed separately below. Additionally, it should be kept in mind that both embodiments lend themselves to scanning with both transmitted and reflected light, either separately or together in the same system.

Diode (or TDI) Array Scanning

Figure 2:
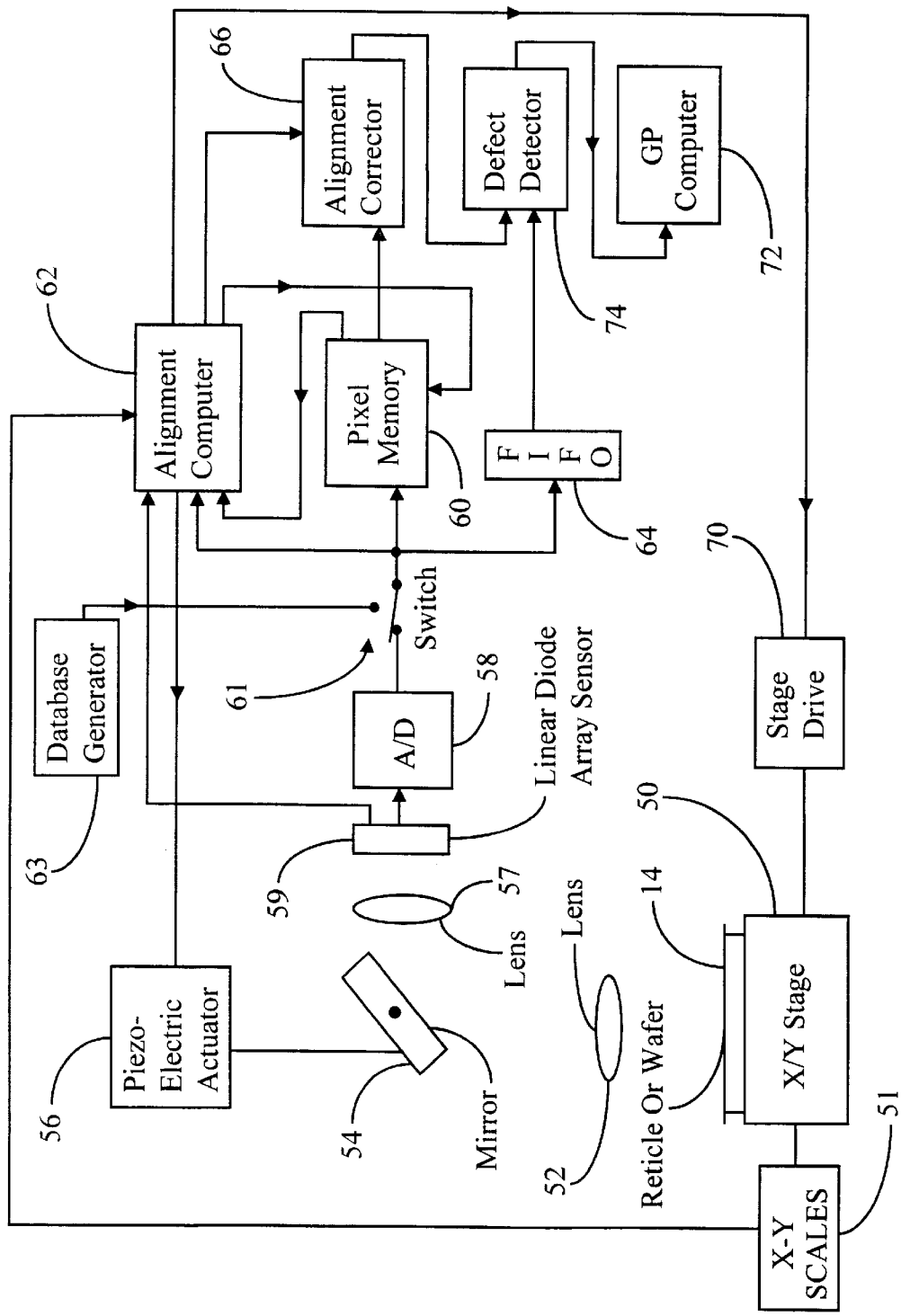
FIG. 2 is a block diagram of a diode array scanning system embodiment of the present invention.

FIG. 2 is a block diagram of a diode (or TDI) array scanning system using reflected light. A wafer, or reticle, 14 is mounted on X/Y stage 50, with X-Y scales 51 mounted thereon to determine stage position, and an illuminator (not shown) illuminates the area of wafer 14 under objective lens 52. The light reflected from wafer 14 travels through objective lens 52, is reflected by tilted mirror 54 to lens 57 through which a portion of the wafer image is projected onto linear diode array 59. Mirror 54 shifts the image of wafer 14 onto diode array 59 by pivoting about an axis perpendicular to the plane of the paper under the control of piezo-electric actuator 56 with the shift occurring in the y-direction. Each time wafer 14 travels the distance of a pixel, array 59 serially reads out a (y-directional) column of intensities which are digitized by A/D converter 58. This information flows from converter 58 into each of pixel memory 60, first-in-first-out (FIFO) memory 64 and alignment computer 62. Pixel memory 60 is a two-dimensional memory of the width of a swath and a length somewhat greater than the widest (x-directional dimension) die to be inspected. Pixel memory 60 is essentially also a FIFO memory, i.e. its input accepts a column of pixels at a time and outputs them at the other end. Pixel memory 60 has output registers which are capable of shifting one pixel, on a command from alignment computer 62, the data in either the x or y direction, prior to producing an output, similar to the method taught by U.S. Pat. No. 4,247,203 by Levy et al. The purpose of pixel memory 60 is to store pixel data from one die while the next die is being scanned so that the two dies can be compared.

This operation is illustrated by the following example. Referring to FIGS. 2 and 3a as die 33 is scanned on the first pass across wafer 14, the information flows into pixel memory 60. Then, as the scanner starts to scan die 35, the information from die 33 is read from pixel memory 60 correctly aligned to the closest integer pixel to the image of die 35. Alignment computer 62 performs a running alignment computation to determine the misalignment between the two data streams corresponding to the first swath across die 33 and the present time swath across die 35. The alignment error of these two data streams is computed as described by Specht. Integer alignment errors are corrected by the output registers of pixel memory 60, while the fractional error is corrected by alignment corrector 66 by using resampling as discussed below.

Overall, the two data streams, one from FIFO memory 64 and the other from alignment corrector 66, arrive at defect detector 74 aligned with a precision of such as $\frac{1}{256}$ of a pixel is achievable.

In addition to the alignment correction commands fed to alignment corrector 66 and pixel memory 60, alignment computer 62 produces three other signals. Two of these, one to stage drive 70 and a second to tilt mirror actuator 56, are intended to provide low frequency alignment correction signals. The signal to tilt mirror actuator 56 provides y-directional control, while the signal to stage drive 70 exercises control in the x-direction. The purpose of these is to make sure that the misalignment between die does not exceed the dynamic range that the correction system can rectify. Alignment computer 62 also produces a strobe signal to initiate the readout of a column of pixels from linear diode sensor 59. Since stage 50 travels approximately at a constant speed, slightly varying the time between strobe pulses allows fine alignment in the x-direction. The strobe is generated in alignment computer 62 by a phase-locked loop which derives its input from the x-directional alignment error and from a linear scale mounted on stage 50 that measures the position of stage 50 by alignment computer 62. U.S. Pat. No. 4,926,489 by Danielson, et al., describes a similar implementation using a phase-locked loop.

FIFO memory 64 is a short memory of the same width as the swath height. Its purpose is to delay the flow of pixel information into defect detector 74 sufficiently to make sure that alignment computer 62 has enough image data to correct the alignment error, prior to the two image data streams reaching defect detector 74.

In defect detector 74 the corresponding intensity values of the two images are compared and if the absolute value of the difference exceeds a predetermined threshold, an error flag is raised. The error data is then sent to general purpose computer 72 (e.g. a Sun workstation), where adjacent defect locations are combined to permit a determination of the size and shape of the defects. This information is then used by yield management programs.

The basic philosophy behind this embodiment of the present invention is that tilting mirror 54 and proper strobing of linear diode sensor 59 provide first order alignment corrections which reduce the needed dynamic range for the fine correction. Since the amount of error contributed by the resampling is a function of the dynamic range of the correction needed, the error intensity into defect detector 74 is smaller than would be achievable without correcting the alignment prior to sampling the image.

In the case where the comparison is die-to-data base, data is obtained from a die 14 on stage 50 with switch 61 in the position shown, then switch 61 is switched to the other position and data from data base generator 63 is connected to supply the second data set. The overall operation is therefore the same as described above.

Figure 2A:
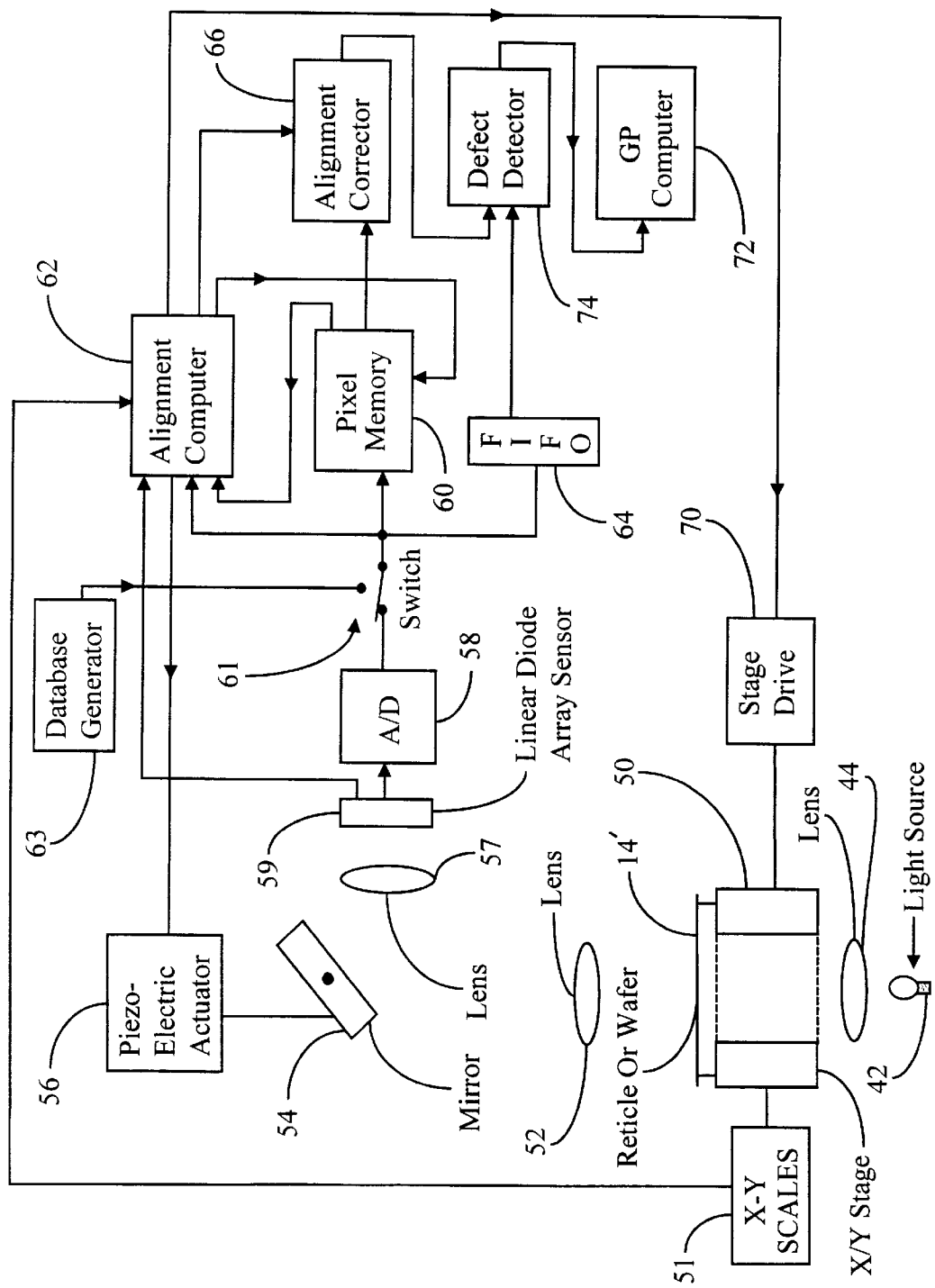
FIG. 2a is the transparent reticle version of the system of FIG. 2.

The subject invention may also be used to inspect transparent substrates, such as a reticle. FIG. 2a illustrates the system in that case. Substrate 14', a reticle, is illuminated from below and the only difference between this implementation and the one that uses transmitted light, is the location of the source of the illumination.

When the reticles, rather than wafers, are inspected, ordinarily the inspection is a comparison with the data base. The data base generator, at its output, produces a data stream that simulates the desired optical image. Switch 61 allows either the datastream from A/D converter 58 or from database generator 63 to flow into pixel memory 60.

Laser Scanning

Figure 4:
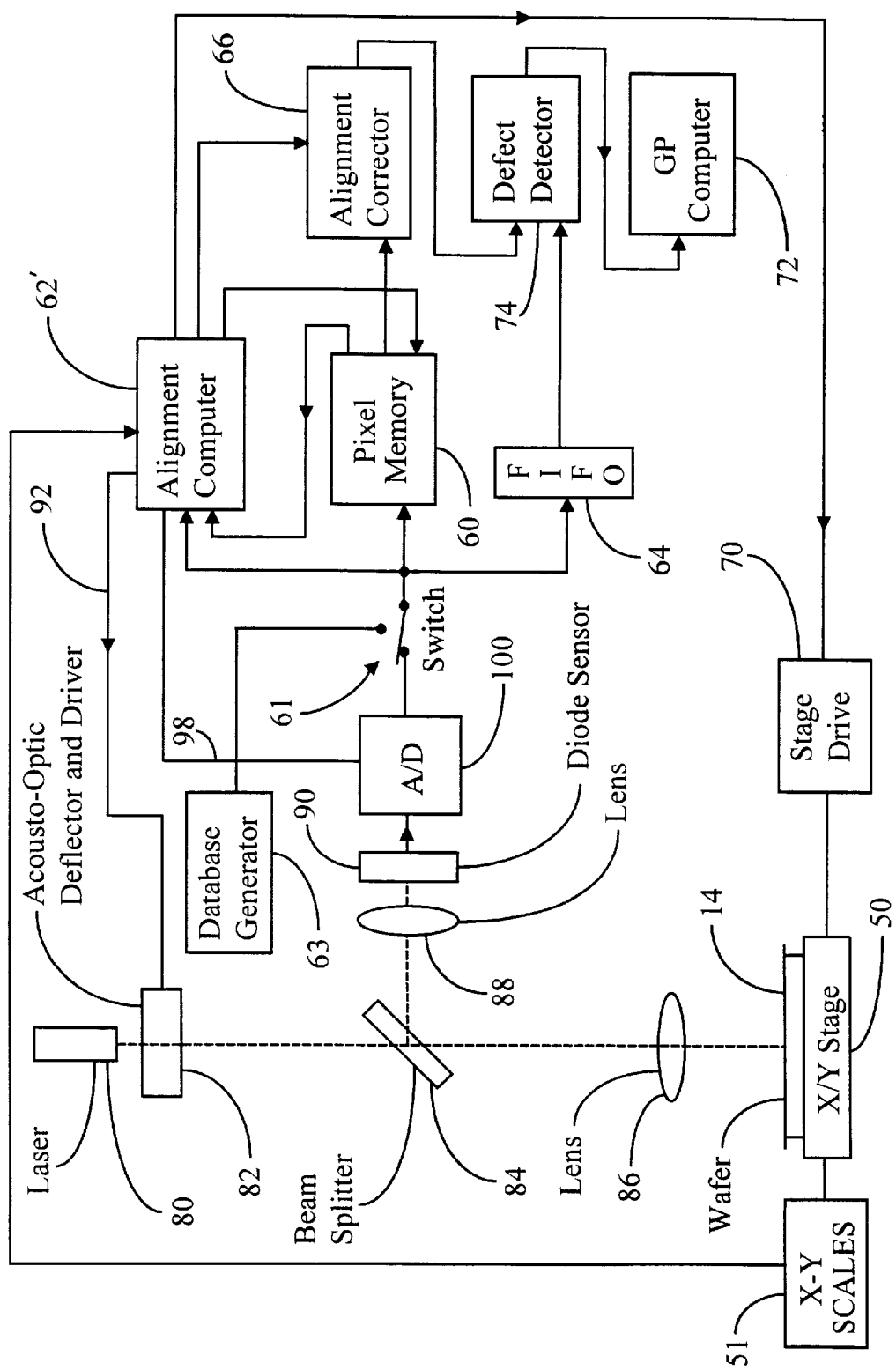
FIG. 4 is a block diagram of a laser scanning system embodiment of the present invention.

The same general approach taught above with respect to FIG. 2 may also be used with laser scanning. The laser scanner here can be adapted from the implementation of the KLA 301 Reticle and Mask Inspection Unit, made by the assignee. FIG. 4 illustrates such a laser scanner embodiment of the present invention. Laser 80 directs coherent light to acousto-optic deflector/driver 82 which deflects the light in the y-direction, as described by Evelet in U.S. Pat. No. 3,851,951 (High Resolution Laser Beam Recorder with Self-focusing Acousto-optic Scanner). The y-deflected light beam from acousto-optic deflector/driver 82 is then applied to beamsplitter 84 through which the laser beam passes and proceeds to lens 86 which focuses the laser beam on wafer 14 on X/Y stage 50. Some of the light incident on wafer 14 is then reflected back into lens 86 and proceeds to beamsplitter 84, where portions of the reflected light are reflected to condenser lens 88 where it is refracted and collected on the surface of single diode sensor 90. The resultant electrical signal from diode 90 is then applied to A/D converter 100. The remaining components of the laser implementation, with the exception of alignment computer 62', function as for the diode array implementation of FIG. 2. Consequently, pixel memory 60, alignment corrector 66, FIFO 64, defect detector 74, general purpose computer 72, stage drive 70 and X/Y stage 50 function as described above for the diode array implementation shown in FIG. 2 with stage 14 executing the same serpentine scanning travel as described previously with respect to FIG. 3.

Figure 5:
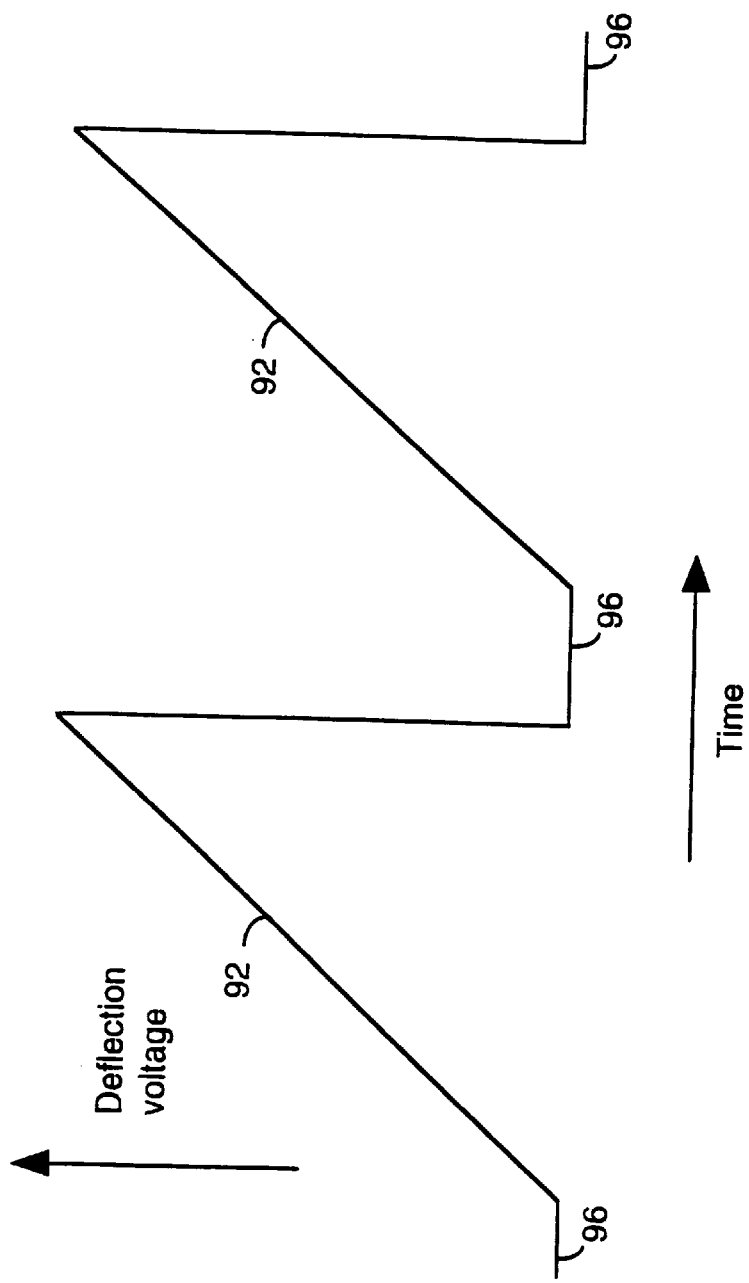
FIG. 5 is a sketch of a signal that is representative of the signal applied to the acousto-optic deflector/driver of FIG. 4 to correct for coarse x-direction mis-alignment of the wafer of the stage.

In addition to the functions outlined above, A/D converter 100 and alignment computer 62' perform additional functions that are necessary to control the operation of acousto-optic deflector/driver 82. Acousto-optic deflector/driver 82 is driven by a saw tooth signal (see FIG. 5) generated by alignment computer 62'. That saw tooth signal includes two components, a ramp 92 and variable time delay 96 between consecutive ramps. X-directional coarse correction is implemented by varying time-delay 96 between successive ramps 92, since the stage travels at a constant speed. The timing of the start of ramp 92 is controlled by a phased-locked loop oscillator of alignment computer 62' that derives its control signal from the x-directional alignment error determined by alignment computer 62'. Alignment computer 62' also generates strobe pulses to control when A/D converter 100 samples the video signal from diode sensor 90. Since the laser beam sweeps across wafer 14 at a constant speed, the y-coordinates of the samples are determined by the timing of the strobe pulses. These strobe pulses are also driven by the phase-locked loop oscillator of alignment computer 62' which is controlled by the y-directional alignment error. The fine corrections in both X and Y are executed in alignment corrector 66, as discussed for the diode array embodiment of FIG. 2.

Also, for the die-to-data base situation, the use of switch 61 and data base generator 63 is as discussed above for FIG. 2.

Figure 4A:
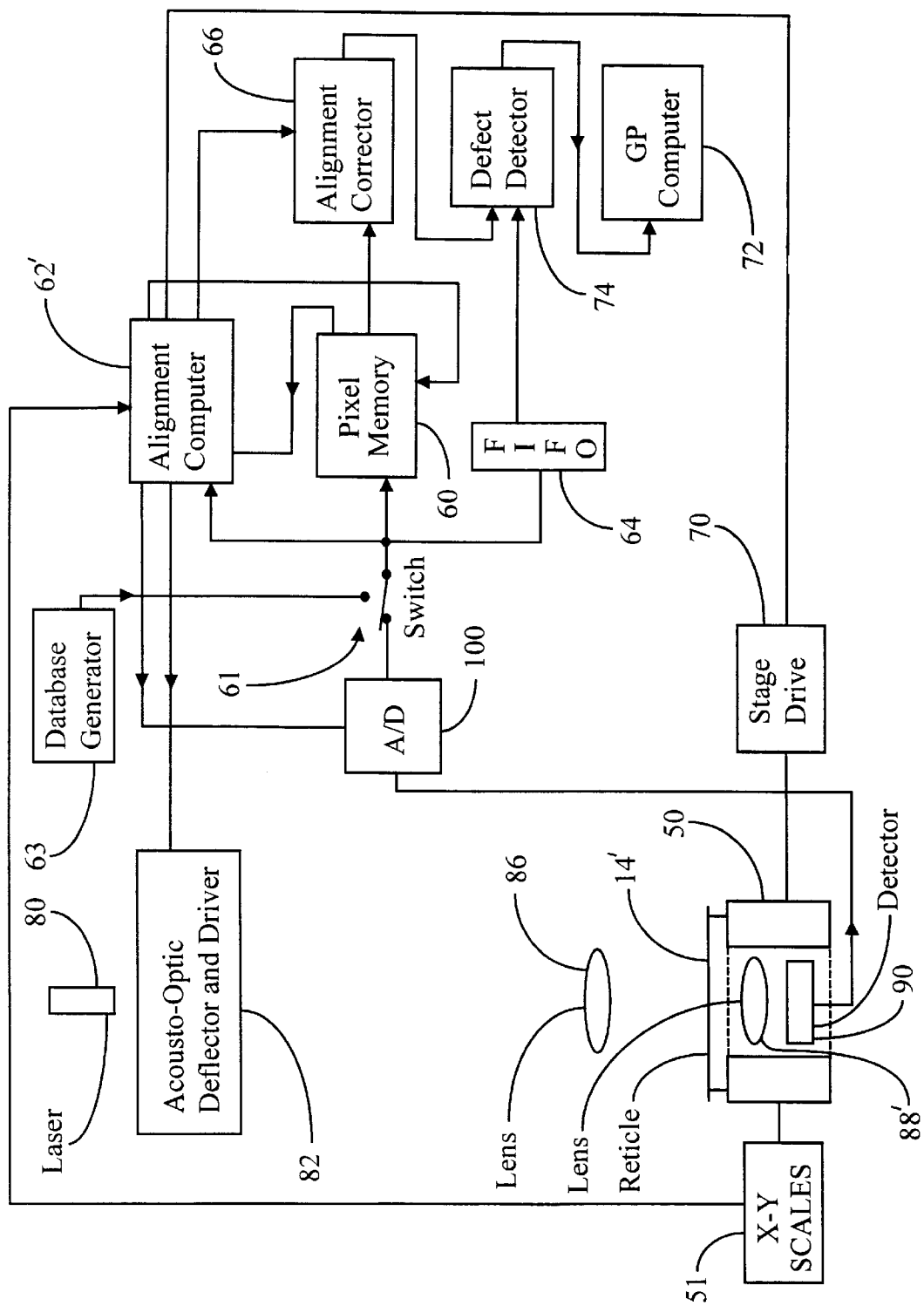
FIG. 4a is the transparent reticle version of the system of FIG. 4.

For the laser scanner implementation using transmitted light as in FIG. 4a, reticle 14' is placed on stage 50 and the implementation is virtually identical to the one shown in FIG. 4 except that diode detector 90 is now under stage 50 to collect, via condenser lens 88'. the light transmitted through reticle 14'. In most instances, the inspection will be against the CADS database for which DataBase Generator 63 provides a simulated image.

While the forgoing techniques are most beneficial in defect detection where image subtraction is used, all known techniques, such as those using feature extraction and comparison, specifically, operate more efficiently when registration errors are minimized. Of course, these methods may also be used when a single image is derived physically and is compared with computer generated data. Furthermore, these alignment techniques are useful in all image processing applications that depend on alignment.

While the present invention has been described in several embodiments and with exemplary routines and apparatus, it is contemplated that persons skilled in the art, upon reading the preceding descriptions and studying the drawings, will realize various alternative approaches to the implementation of the present invention. It is therefore intended that the following appended claims be interpreted as including all such alterations and modifications that fall within the true spirit and scope to the present invention and the appended claims.

What is claimed is:

1. A method for providing a coarse alignment between a first image signal and a second image signal for a substrate on an x/y stage of an inspection machine defining x and y directions, said inspection machine having a fixed pixel size and pixel grid that is correlated to positions of said x/y stage, for each selected x position in the x direction during scanning of said substrate, said substrate in the y direction, said coarse alignment method comprising the steps of:

a. storing a first swath signal of said first image signal in a first memory;

b. determining x and y position coordinates in the x and y directions, respectively, of a first pixel of said first swath signal of said first image signal of step a. relative to boundaries of a pixel of said pixel grid;

c. scanning across a first pattern on said substrate to determine a first swath signal of said second image signal;

d. determining x and y position coordinates of a first pixel of said first swath signal of said second image signal detected in step c. relative to the boundaries of a pixel of said pixel grid in which said first pixel of said first swath of said second image signal is detected;

e. calculating the positional offset of said x and y coordinates of said first pixel of said first swath of said second image signal within said pixel of said pixel grid of step d. from said x and y coordinates of said first pixel of said first image signal within said pixel of said pixel grid from step b.; and f. performing a running alignment of said first pixel of each swath signal of said second image signal within said pixel grid in relation to said first pixel of said first image signal using said positional offset calculated in step e. by advancing or retarding said x path to correct for said x positional offset, and advancing or retarding the scan in the y direction to correct for said y positional offset to realign each swath signal of said second image signal with each swath signal of said first image signal.

2. A method as in claim 1 wherein said first image signal of step a. is stored in a database.

3. A method as in claim 1 wherein:

said method, preceding step a., further includes the step of:

g. sequentially scanning swaths across a first pattern on said substrate to determine each swath signal of said first image signal; and said said pattern in step c. is a second pattern on said substrate.

4. A method as in claim 3 wherein in step b. said x and y position coordinates of said first pixel of said first image signal is relative to the boundaries of said first pixel grid pixel in which said first pixel of said first image signal is detected.

5. A method as in claim 1 wherein in step f.:

scanning in said y direction is performed by varying the angle of a tilt mirror; and said advancing or retarding the scan in the y direction is performed by advancing or retarding the angle of said tilt mirror.

6. A method as in claim 1 wherein in step f.:

scanning in said y direction is performed by varying the time delay of a laser; and said advancing or retarding the scan in the y direction is performed by advancing or retarding the time delay of said laser.

7. An apparatus to provide coarse alignment between a first image signal with a second image signal of a pattern on a substrate, to generate an image pattern said apparatus comprising:

an x-y stage defining x and y directions to transport said substrate with a fixed pixel size and pixel grid that is correlated to positions of said x/y stage;

a scanner to image said pattern on said substrate in sequential swaths, and to generate electronic sequential swath signals of said second image signal as said substrate is scanned in said y direction at successive x locations of said pattern;

a FIFO memory coupled to said scanner to sequentially receive said swath signals of said second image signal;

a pixel memory to receive, and store therein, sequential swath signals of said first image signal;

an alignment computer:

coupled to said pixel memory to receive a first swath signal of said first image signal therefrom for performing a first process step of determining x and y position coordinates of a first pixel of said first swath signal of said first image signal relative to boundaries of a pixel of said pixel grid;

coupled to said scanner to sequentially receive swath signals of said second image signal therefrom and to perform a second process step of determining x and y position coordinates of a first pixel of said first swath signal of said second image signal relative to the boundaries of a pixel of said pixel grid in which said first pixel of said first swath of said second image signal is detected;

performing a third process step of calculating the positional offset of said x and y coordinates of said first pixel of said first swath signal of said second image signal within said pixel of said pixel grid in which said first pixel of said first swath signal of said second image signal is detected from said x and y coordinates of said first pixel of said first image signal within said pixel of said pixel grid in which said first pixel of said first swath signal of said first image signal is detected; and an alignment corrector coupled to said alignment computer to receive said positional offset and coupled to said pixel memory:

performing a fourth process step of a running alignment of said first pixel of each swath signal of said second image signal within said pixel grid in relation to said first pixel of said first image signal using said positional offset of said third process step by advancing or retarding the scan in said x direction to correct for said x positional offset, and advancing or retarding the scan in the y direction to correct for said y positional offset, to realign each swath signal of said second image signal with each swath signal of said first image signal.

8. An apparatus as in claim 7 wherein:

said apparatus further includes a sensor disposed to receive from said scanner, and to convert, said imaged pattern to said second image signal; said scanner includes:

a tilt mirror having an axis of rotation in the y direction to reflect said pattern from said substrate to said sensor; and a mirror position actuator coupled to said tilt mirror and said alignment computer to control the position of said tilt mirror in response to a signal from said alignment computer to shift the x position of said second image signal with respect to the x position of said first image signal.

9. An apparatus as in claim 8 wherein:
said substrate is partially transparent having a first and a second surface, with said first surface closest to said tilt mirror; and
said apparatus further includes a light source spaced apart from said second surface of said substrate.

10. An apparatus as in claim 8 wherein:
said pattern is a second pattern on said substrate; and
said tilt mirror also reflects a first pattern from said substrate to said sensor.

11. An apparatus as in claim 7 wherein said scanner includes:
a laser positioned to direct a laser beam toward a surface of said substrate;
an acusto-optic deflector/driver positioned between said laser and said substrate and coupled to said alignment computer to shift the position of said laser beam on said surface of said substrate in response to a signal from said alignment computer to shift the x position of said second optical image with respect to the x position of said first pixel of said first swath signal of said first image signal; and
a beamsplitter positioned between said acusto-optic deflector/driver and said substrate to pass therethrough said laser beam from said acusto-optic deflector/driver to said substrate and to reflect light reflected from said surface of said substrate to said scanner.

12. An apparatus as in claim 7 wherein:
said substrate is partially transparent having a first and a second surface;
said scanner includes:
a laser positioned to direct a laser beam toward said first surface of said substrate; and
an acusto-optic deflector/driver positioned between said laser and said substrate and coupled to said alignment computer to shift the position of said laser beam on said surface of said substrate in response to a signal from said alignment computer to shift the x position of said second image signal with respect to the x position of said first image signal; and
said apparatus further includes a sensor spaced-apart from said second surface of said substrate disposed to receive from said scanner, and to convert, said imaged pattern to said second image signal.

13. An apparatus as in claim 7 wherein:
said pattern is a second pattern;
said scanner serially obtains a first image signal from a first pattern on said substrate as a first sequence of swath images and said second image signal from said second pattern on said substrate as a second sequence of swath images, with a time delay between receipt of corresponding swath images of said first and second sequences of swath images;
said scanner serially receives said sequences of said first and second swath images interlaced with each other and serially converts said interlaced sequences of first and second swath images of said first and second image signals with said time delay between each corresponding pair of swath signals; and
said alignment computer receives said first swath signals of said first image signal from said pixel memory.

14. An apparatus as in claim 7 wherein said pixel memory is a database into which said first image signal is prestored.

15. An apparatus to inspect a substrate utilizing a first image signal and a second image signal of a pattern on said substrate, to generate an image pattern said apparatus comprising:

an x-y stage defining x and y directions to transport said substrate with a fixed pixel size and pixel grid that is correlated to positions of said x-y stage;
a scanner to image said pattern on said substrate in sequential swaths, and to generate electronic sequential swath signals of said second image signal as said substrate is scanned in said y direction at successive x locations of said pattern;
a FIFO memory coupled to said scanner to sequentially receive said swath signals of said second image signal;
a pixel memory to receive, and store therein, sequential swath signals of said first image signal;
an alignment computer:
coupled to said pixel memory to receive a first swath signal of said first image signal therefrom for performing a first process step of determining x and y position coordinates of a first pixel of said first swath signal of said first image signal relative to boundaries of a pixel of said pixel grid;
coupled to said scanner to sequentially receive swath signals of said second image signal therefrom and to perform a second process step of determining x and y position coordinates of a first pixel of said first swath signal of said second image signal relative to the boundaries of a pixel of said pixel grid in which said first pixel of said first swath of said second image signal is detected;
performing a third process step of calculating the positional offset of said x and y coordinates of said first pixel of said first swath signal of said second image signal within said pixel of said pixel grid in which said first pixel of said first swath signal of said second image signal is detected from said x and y coordinates of said first pixel of said first image signal within said pixel of said pixel grid in which said first pixel of said first swath signal of said first image signal is detected;
an alignment corrector coupled to said alignment computer to receive said positional offset and coupled to said pixel memory:
performing a fourth process step of a running alignment of said first pixel of each swath signal of said second image signal within said pixel grid in relation to said first pixel of said first image signal using said positional offset of said third process step by advancing or retarding the scan in said x direction to correct for said x positional offset, and advancing or retarding the scan in the y direction to correct for said y positional offset, to realign each swath signal of said second image signal with each swath signal of said first image signal; and
a defect detector coupled to said alignment corrector and said FIFO memory to detect and identify defects in said second image signal as aligned by comparison with said first image signal.

16. An apparatus as in claim 15 wherein:
said apparatus further includes a sensor disposed to receive from said scanner, and to convert, said image of said pattern to said second image signal;
said pattern is a second pattern;
said scanner serially obtains a first image signal from a first pattern on said substrate and said second image signal from said second pattern on said substrate, with a time delay between receipt of said first and second image signals;
said sensor serially receives said first and second optical images from said scanner and serially converts said first and second optical images to said first and second image signals with said time delay therebetween;

said memory is a pixel memory having serially connected first and second sections, each of said first and second sections having an input port and an output port, with the input port of said first section being an input port of said pixel memory, the output port of said first section being a first output port of said pixel memory and connected to the input port of said second section, and the output port of said second section form a second output port of said pixel memory, said first section having a fixed length and said second section having a controllable length ranging from zero to n integer pixel units, said input port of said pixel memory coupled to said sensor to serially receive said first and second image signals; and said alignment computer receives said first image signal from said pixel memory.

17. An apparatus as in claim 15 wherein said pixel memory is a database into which said first image signal is prestored.

18. An apparatus as in claim 15 wherein:

said apparatus further includes a sensor disposed to receive from said scanner, and to convert, said imaged pattern to said second image signal;

said scanner includes:
- a tilt mirror having an axis of rotation in the y direction to reflect said pattern from said substrate to said sensor; and
- a mirror position actuator coupled to said tilt mirror and said alignment computer to control the position of said tilt mirror in response to a signal from said alignment computer to shift the x position of said pattern with respect to the x position of said first image signal.

19. An apparatus as in claim 18 wherein:

said substrate is partially transparent having a first and a second surface, with said first surface closest to said tilt mirror; and said apparatus further includes a light source spaced apart from said second surface of said substrate.

20. An apparatus as in claim 18 wherein:

said pattern is a second pattern on said substrate; and a tilt mirror also reflects said first pattern from said substrate to said sensor.

21. An apparatus as in claim 15 wherein:

said apparatus further includes a sensor disposed to receive from said scanner, and to convert, said image of said pattern to said second image signal;

said scanner includes:
- a laser positioned to direct a laser beam toward a surface of said substrate;
- an acusto-optic deflector/driver positioned between said laser and said substrate and coupled to said alignment computer to shift the position of said laser beam on said surface of said substrate in response to a signal from said alignment computer to shift the x position of said second optical image with respect to the x position of said first image signal; and
- a beamsplitter positioned between said acusto-optic deflector/driver and said substrate to pass therethrough said laser beam from said acusto-optic deflector/driver to said substrate and to reflect light reflected from said surface of said substrate to said sensor.

22. An apparatus as in claim 15 wherein:

said substrate is partially transparent having a first and a second surface;

said scanner includes:
- a laser positioned to direct a laser beam toward said first surface of said substrate; and
- an acusto-optic deflector/driver positioned between said laser and said substrate and coupled to said alignment computer to shift the position of said laser beam on said surface of said substrate in response to a signal from said alignment computer to shift the x position of said second image signal with respect to the x position of said first image signal; and said apparatus further includes a sensor spaced-apart from said second surface of said substrate disposed to receive from said scanner, and to convert, said imaged pattern to said second image signal.

23. An apparatus as in claim 15 wherein:

said scanner includes a tilt mirror to scan said pattern in said y direction by varying the angle of said tilt mirror; and said advancing or retarding the scan in the y direction is performed by advancing or retarding the angle of said tilt mirror under control of said alignment corrector.

24. A method for inspecting a substrate utilizing a first image signal and a second image signal of a pattern on said substrate with said substrate on an x/y stage of an inspection machine, said inspection machine having a fixed pixel size and pixel grid that is correlated to positions of said x/y stage defining x and y directions, for each selected x position in the x direction during scanning of said substrate, a swath is scanned across said substrate in the y direction, said inspection method comprising the steps of:

a. storing a first swath signal of said first image signal in a first memory;

b. determining x and y position coordinates in the x and y directions, respectively, of a first pixel of said first swath signal of said first image signal of step a. relative to boundaries of a pixel of said pixel grid;

c. scanning a first swath across said pattern on said substrate to determine a first swath signal of said second image signal;

d. determining x and y position coordinates of a first pixel of said first swath signal of said second image signal detected in step c. relative to the boundaries of a pixel of said pixel grid in which said first pixel of said first swath of said second image signal is detected;

e. calculating the positional offset of said x and y coordinates of said first pixel of said first swath of said second image signal within said pixel of said pixel grid of step d. from said x and y coordinates of said first pixel of said first image signal within said pixel of said pixel grid from step b.;

f. performing a running alignment of said first pixel of each swath signal of said second image signal within said pixel grid in relation to said first pixel of said first image signal using said positional offset calculated in step e. by advancing or retarding said x path to correct for said x positional offset, and advancing or retarding the scan in the y direction to correct for said y positional offset to realign each swath signal of said second image signal with each swath signal of said first image signal;

g. sequentially storing each swath signal of said first image signal in said first memory;

h. sequentially scanning said substrate and storing each realigned swath signal of said second image signal in a second memory; and i. sequentially comparing each swath signal of said first image signal with a corresponding realigned swath signal of said second image signal to determine if defects are present in said pattern on said substrate that corresponds to said second image signal.

25. A method as in claim 24 wherein:

said method, preceding step a., further includes the step of:

j. sequentially scanning swaths across a first pattern on said substrate to determine each swath signal of said first image signal; and said pattern in step c. is a second pattern.

26. A method as in claim 25 wherein in step b. said x and y position coordinates of said first pixel of said first image signal is relative to the boundaries of said first pixel grid pixel in which said first pixel of said first image signal is detected.

27. A method as in claim 24 wherein in step f.:

scanning in said y direction is performed by varying the time delay of a laser; and said advancing or retarding the scan in the y direction is performed by advancing or retarding the time delay of said laser.

28. A method as in claim 24 wherein said first image signal of step a. is stored in a database.

* * * * *